US008665433B2

(12) United States Patent
Da Re et al.

(10) Patent No.: US 8,665,433 B2
(45) Date of Patent: Mar. 4, 2014

(54) STANDOFF EXPLOSIVES DETECTOR USING DEEP-UV RAMAN SPECTROSCOPY (75) Inventors: Ryan E. Da Re, Bristow, VA (US); Howard N. LaValley, Albuquerque, NM (US); Jeromy Paul Rezac, Bel Air, MD (US); James E. Pendell Jones, Baltimore, MD (US)

(73) Assignee: Exelis Inc., McLean, VA (US)

( * ) Notice: Subject to any disclaimer, the term of this patent is extended or adjusted under 35 U.S.C. 154(b) by 324 days.

(21) Appl. No.: 13/150,757

(22) Filed: Jun. 1, 2011

(65) Prior Publication Data

US 2012/0044478 A1 Feb. 23, 2012

Related U.S. Application Data (60) Provisional application No. 61/374,465, filed on Aug. 17, 2010.

(51) Int. Cl.
*G01J 3/44* (2006.01)

(52) U.S. Cl.
USPC ........................................ 356/301

(58) Field of Classification Search
CPC ......... G01J 3/44; G01J 3/4406; G01J 3/4412; G01N 21/65; G01N 21/658
USPC ........................................ 356/301
See application file for complete search history.

(56) References Cited

U.S. PATENT DOCUMENTS

| 3,403,061 | A  | * | 9/1968  | McDonald ..................... 149/7 |
| 6,205,354 | B1 | * | 3/2001  | Gellermann et al. ......... 600/477 |
| 6,608,677 | B1 | * | 8/2003  | Ray et al. ..................... 356/301 |
| 7,383,129 | B1 |   | 6/2008  | Baillot et al. |
| 7,760,352 | B2 | * | 7/2010  | Armstrong et al. ........... 356/301 |
| 8,072,595 | B1 | * | 12/2011 | Bastiaans et al. ............. 356/301 |
| 8,159,662 | B2 | * | 4/2012  | Rezac et al. ................... 356/301 |
| 2003/0146281 | A1 | * | 8/2003 | Hodges ......................... 235/454 |
| 2007/0002319 | A1 |   | 1/2007 | Knopp et al. |
| 2007/0165236 | A1 | * | 7/2007 | Haridas ......................... 356/451 |
| 2007/0222981 | A1 |   | 9/2007 | Ponsardin et al. |
| 2010/0171951 | A1 | * | 7/2010 | Misra et al. ................... 356/301 |
| 2012/0035442 | A1 | * | 2/2012 | Barman et al. ................ 600/316 |

FOREIGN PATENT DOCUMENTS

WO    2007032814 A2    3/2007

OTHER PUBLICATIONS

W.F. Hug et al., "Performance Status of a Small Robot-Mounted or Hand-Held, Solar-Blind, Standoff Chemical, Biological, and Explosives (CBE) Sensor", Proceedings of SPIE, vol. 7304, Jan. 1, 2009, pp. 73040Z-73040Z-8.

European Search Report EP11 17 7529, Nov. 9, 2011 received in counterpart application No. EP 2 420 823 A1.

(Continued)

*Primary Examiner* — Gregory J Toatley
*Assistant Examiner* — Shawn Decenzo
(74) *Attorney, Agent, or Firm* — Edell, Shapiro & Finnan, LLC (57) ABSTRACT A method of performing Raman spectroscopy, and an apparatus for performing the method, including irradiating, with laser light, a trace amount of a target substance disposed on a painted surface, receiving reflected laser light and a Raman return signal from the trace amount of the target substance, processing the Raman return signal using, at least, a spectrograph and camera to obtain a Raman signature for the target substance, and identifying the target substance based on the Raman signature for the target substance and a database of Raman signatures. The laser light wavelength may be selected based on a ratio of Raman return signal power to fluorescence power.

20 Claims, 8 Drawing Sheets

(56) References Cited

OTHER PUBLICATIONS

Carter et al., "Standoff Detection of High Explosive Materials at 50 Meters in Ambient Light Conditions Using a Small Raman Instrument," Applied Spectroscopy, vol. 59, No. 6, (2005), pp. 769-775.

Chyba et al., "Optimization of a chemical identification algorithm," SPIE 7698-09 (2010), Apr. 6, 2010, pp. 1-27.

Comanescu et al., "Identification of Explosives with Two-Dimensional Ultraviolet Resonance Raman Spectroscopy", Applied Spectroscopy, vol. 62, No. 8 (2008), pp. 833-839.

Gaft et al., "UV gated Raman spectroscopy for standoff detection of explosives", Elsevier (2008), pp. 1739-1746.

Lewis et al., "Interpretation of Raman Spectra of Nitro-Containing Explosive Materials. Part I: Group Frequency and Structual Class Membership", Applied Spectroscopy, vol. 51, No. 12 (1997), pp. 1854-1867.

Misra et al., "Compact standoff Raman system for detection of homemade explosives", SPIE, vol. 7665, (2010), pp. 1-11.

Moros et al., "Simultaneous Raman Spectroscopy-Laser-Induced Breakdown Spectroscopy for Instant Standoff Analysis of Explosives Using a Mobile Integrated Sensor Platform", Analytical Chemistry, vol. 82, No. 4, Feb. 15, 2010, pp. 1389-1400.

Nagli et al., "Absolute Raman cross-sections of some explosives: Trend to UV", Elsevier (2007), pp. 1-8.

Pettersson et al., "Explosives Standoff Detection Using Raman Spectroscopy; From Bulk Towards Trace Detection", SPIE, vol. 7664, (2010), pp. 1-12.

Pinkham et al., "(U) Investigation and field-testing of laser-based standoff explosive detection technologies", Feb. 23, 2010, (16 pages).

Sands et al., "UV-Excited Resonance Raman Spectroscopy of Narcotics and Explosives", Journal of Forensic Sciences, 1998; 43(3): pp. 509-513.

Sharma et al., "Stand-off Raman Instrument for Detection of Bulk Organic and Inorganic Compounds", SPIE, vol. 6554, 655405, (2007), (12 pages).

Tuschel et al., "Deep Ultraviolet Resonance Raman Excitation Enables Explosives Detection", Applied Spectroscopy, vol. 64, No. 4 (2010, pp. 425-432.

Benthem et al., "Fast algorithm for the solution of large-scale non-negativity-constrained least squares problems", Journal of Chemometrics 2004; 18: pp. 441-450.

Waterbury et al., "Results of a UV TEPS/Raman System for Standoff Detection of Energetic Materials", pp. 1-4.

Analytical Sensitivity-Evaluation Report, May 2003, (32 pages).

Ray et al., Ultraviolet mini-Raman lidar for stand-off, in situ identification of chemical surface contaminants, Review of Scientific Instruments, AIP, Melville, NY, US, vol. 71, No, 9; pp. 3485-3489, Sep. 2000.

Sharma et al., Portable remove Raman system for monitoring hydrocarbon, gas hydrates, and explosives in the environment, Spectrochimica Acta, Part A: Molecular and Biomolecularspectroscopy, Elsevier, Amsterdam, NL, vol. 61, No. 10, Aug. 1, 2005, pp. 2404-2412.

Carter et al., Stand-off Raman detection using dispersive and tunable filter based systems, Spectrochimica Acta. Part A: Molecular and Biomolecularspectroscopy, Elsevier, Amsterdam, NL, vol. 61, No. 10, Aug. 1, 2005, pp. 2288-2298.

Sharma et al., Remote Pulsed Raman Spectroscopy of Inorganic and Organic Materials to a Radial Distance of 100 Meters, Applied Spectroscopy, (online), vol. 60, No. 8, 2006, pp. 871-876.

Blanco et al., UV Raman Detection of 2,4-DNT in contact with Sand Partiacles, Proc. of Spie, (online), vol. 6217, 2006, pp. 621737-1-621737-10.

Gardner et al., Remote chemical biological and explosive agent detection using a robot-based Raman detector; Proc Spie (online), vol. 6962, Apr. 16, 2008, pp. 69620T-1-69620T-10.

* cited by examiner

STANDOFF EXPLOSIVES DETECTOR USING DEEP-UV RAMAN SPECTROSCOPY

This application claims the benefit of U.S. Provisional Application No. 61/374,465, filed Aug. 17, 2010, which is incorporated herein by reference in its entirety.

FIELD OF THE INVENTION

The present invention is related to Raman spectroscopy, and more particularly to systems and methods for performing stand-off Raman spectroscopy using laser light in the deep ultraviolet spectral region.

BACKGROUND OF THE INVENTION

The danger of exposure to chemical or biological agents can be severe. Whether a result of unintended release, by way of, e.g., an accident, or a result of intentional delivery, it is desirable to quickly and accurately identify (1) the type of agent that has been released and (2) the precise area of contamination. Early and accurate detection of such dangerous substances can be a significant factor in reducing potential casualties and limiting further spreading of the agent, e.g., by wind, human and animal contact, etc.

It is likewise important to be able to quickly and accurately identify the presence of explosive materials. Such detection is particularly important in security and military settings. The sooner detection can take place, the sooner personnel can be evacuated or other appropriate measures taken.

Prior remote sensor technologies designed to measure surface-deposited chemical contamination used vehicles and associated test equipment that retrieved a physical sample of the contaminant and then used an extremely cumbersome and time-consuming process to analyze the sample, e.g., a mechanical sampling wheel system coupled with a mass spectrometer to test for chemical agents.

In view of the complexity of such approaches, newer, simpler technologies were desired. One emerging technology in response to this desire is referred to, generally, as "standoff surface detection," and refers to a category of technologies that permit detection of a substance without actually having to physically come in contact with the substance. The goal of these detection systems is to provide the capability to detect, identify, locate, quantify, warn, and report chemical and biological threats and thereby give military forces or civilian personnel sufficient early warning to avoid (further) contamination and deploy appropriate counter measures.

One of the technologies that enables standoff surface detection is Raman spectroscopy. Raman spectroscopy is a technique used to characterize materials and thereafter to identify such materials. Typically, a laser transmitter serves as a spectrally narrow light source with high irradiance. The laser illuminates a known or an unknown substance, such as a chemical compound, biological agent, or explosive material, among others. A portion of the incident light is Raman scattered by the substance. This light is scattered in all spatial directions as well as shifted spectrally to discrete wavelengths. These wavelength shifts correspond to unique vibrational energies associated with the molecular bonds in the substance.

In conventional standoff Raman spectroscopy systems, the Raman scattered light is collected by a telescope and is coupled into a dispersive optical system. The telescope focuses the collected light onto, e.g., an optical fiber bundle. At the opposite end of the fiber bundle, individual fibers are oriented linearly to form an entrance slit for a grating-based spectrograph. An electro-optical detector array records the optical spectrum of the Raman scattered light. This spectrum serves as a "fingerprint" for the known or unknown substance. An analysis computer stores the reference spectral information along with information identifying the known substance, and more often, employs pattern-matching algorithms to identify the unknown substance from a spectral library of previously analyzed and "fingerprinted" reference substances.

Laboratory-based Raman spectroscopy systems have been in use for many years. Recently, portable Raman systems have become possible as a result of components that have decreased in size and unique integration techniques. A description of one such portable system can be found in U.S. Pat. No. 6,608,677, which is incorporated herein by reference. A backpack implemented man-portable Raman sensor has also recently been fielded by ITT (Wilmington, Del.). Aspects of that system are described in U.S. Pat. No. 7,796,251, entitled Method, Apparatus and System for Rapid and Sensitive Standoff Detection of Surface Contaminants, which is also incorporated herein by reference. Truck mounted Raman sensors have also been fielded to date. Reference may also be made to U.S. Pat. No. 6,788,407, also incorporated herein by reference, for still further discussion of Raman spectrometry.

Notwithstanding these known systems, there remains a need to provide different forms of Raman sensors to meet the needs of both civilian and military personnel responsible for identifying, especially, trace amounts or residues of explosive substances.

SUMMARY OF INVENTION EMBODIMENTS

The present invention provides a unique implementation of a Raman spectroscopy system that can be employed to avoid having to be in the immediate vicinity of dangerous substances or items. More specifically, with embodiments in accordance with the present invention, personnel are provided the capability to perform remote yet sensitive site exploitation including inspection of buildings, equipment, vehicles, aircraft, and other manmade or natural surfaces for the presence of unknown substances or items including, but not limited to, explosive material (e.g., TNT and RDX), homemade explosives and their precursors, and chemicals including chemical warfare agents (CWAs), and toxic industrial chemicals (TICs). One significant advantage of embodiments of the present invention is the ability to search for and detect improvised explosive devices (IEDs) or traces of explosives on vehicles without having to place personnel in the same location in which explosives might be hidden.

Other advantages of embodiments of the present invention include the fact that the technology (1) is a non-contact standoff system, (2) allows mapping of the surface contamination, and (3) provides quick response (typically only seconds to perform detection).

These and other features of embodiments of the present invention and their attendant advantages will be more fully appreciated upon a reading for the following detailed description in conjunction with the associated drawings.

DETAILED DESCRIPTION

Raman signatures tend to be distinctive and unique to a material; thus this "optical fingerprinting" technique for identifying explosives at standoff distances has received much attention. Raman signals can be generated with laser excitation, and numerous studies have been conducted to evaluate Raman spectroscopy for explosives detection in the near-infrared, visible, and UV spectral regions. This flexibility has spurred the development of Raman systems, some capable of detecting explosives from tens of meters.

In this regard, many academic studies have focused on only one aspect of Raman spectroscopy for explosives detection, such as demonstrating the feasibility of long standoff distances or the potential of a particular dual-sensor concept. By and large, these studies have been performed under experimental conditions that are not particularly analogous to real-world field operations. For example, the study presented in Pettersson, A.; Wallin, S.; Östmark, H.; Ehlerding, A.; Johansson, I.; Nordberg, M.; Ellis, H.; Al-Khalili, A. *Proc. of SPIE,* 2010, 7664, 76641K-1 demonstrated that ammonium nitrate (AN) can be detected outdoors from a distance of 470 meters with a 532-nm Raman system, but the data were recorded using essentially laboratory conditions. Specifically, a 500-mL container of bulk AN was interrogated for a period of 1-10 seconds with pulse energies of 320 mJ at a repetition rate of 10 Hz (i.e., ~3.2 Watts of laser power).

Increasing the distance and detecting many types of explosives at very low concentrations continues to be an area of interest. Described herein is a UV Raman sensor that has been shown to detect TNT, PETN, and AN at concentrations as low as 3-50 $\mu g/cm^2$ from a standoff distance of 10 meters using moderate laser power (~100 mW). Importantly, this level of sensitivity has been demonstrated for explosive residues on field relevant backgrounds in a timeframe on the order of seconds. These are key points because real-world backgrounds such as painted surfaces of vehicle panels often limit the sensitivity of Raman spectroscopy by overwhelming the Raman signal with fluorescence. Furthermore, the choice of excitation wavelength is related to the amount of material present.

Detecting some explosives can be particularly challenging because Raman scattering from these materials is insufficient to overcome the limitations imposed by absorption. In general, strong absorption limits penetration into the target by the incident laser beam, minimizing the volume of material that can contribute to the Raman signal. The emerging Raman signal is also absorbed by the target along its path to the receiver. Consequently, the amount of material that can contribute to the observed Raman signal is limited to a thin layer for strongly absorbing explosives. RDX and HMX absorb strongly between 225 nm and 275 nm, and the thickness of material that contributes to the signal is predicted to be less than 0.3 μm (for 257-nm excitation). Ultimately, signal strength depends on the efficiency of Raman scattering as well as absorption. For example, because Raman scattering from TNT is ~100× greater than from RDX with 257-nm excitation, Raman signals obtained from TNT are considerably larger than those from RDX, despite the fact that absorption limits the theoretical interaction depth for TNT to ~100 nm.

Embodiments of the present invention use a deep UV laser to generate Raman scattering from the surface chemical. Raman scattering is generally much stronger with UV laser light than with visible and IR light due to the well-known $v^4$ effect and the onset of a phenomenon known as resonance enhancement. Importantly, unlike the Raman signals obtained with visible and IR lasers, resonance enhancement tends to emphasize the spectral features of the targeted explosives as compared to the spectral features obtained from the background, making it possible to detect small quantities of explosives. Moreover, the system is solar blind and interference from background fluorescence is minimal. A single-frequency laser can be employed, and processing does not require picture-to-picture registration is required for differential imaging techniques.

Figure 1:
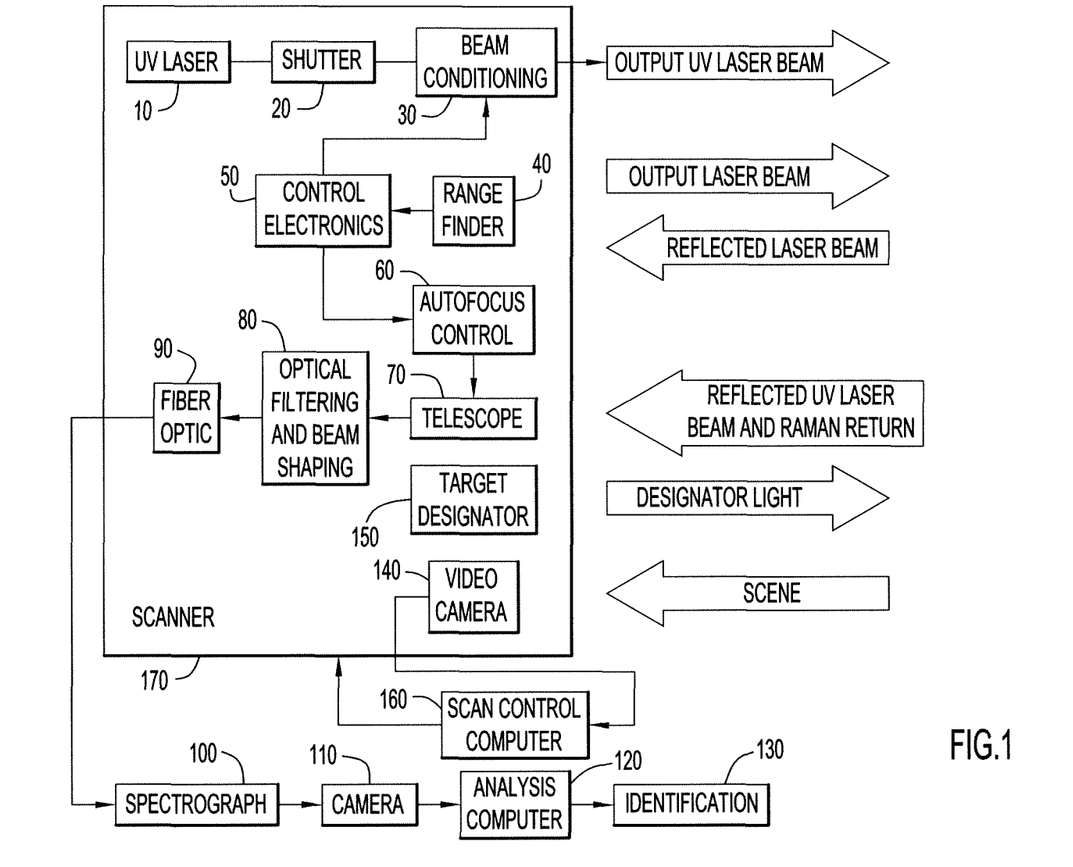
FIG. 1 is a schematic functional diagram of a Raman spectroscopy system in accordance with an embodiment of the present invention.

FIG. 1 depicts a Raman spectroscopy system in accordance with one possible implementation of the present invention. A scanner 170 includes a UV laser 10 that is tuned to a single frequency in the wavelength region below 400 nm, preferably below 250 nm, and more preferably around 248 nm in order to avoid fluorescence from relevant surfaces, as will be discussed in more detail below. The laser's outgoing UV beam is permitted to radiate to a target substance via a safety shutter 20 and beam conditioning optics 30. The beam conditioning optics 30 adjust the beam's characteristics to match the interrogation spot size of a receiver telescope 70. This beam radiates from the system to a surface on which trace amounts of, e.g., an unknown chemical, such as an explosive material or precursor, have been deposited. The phrase "trace amounts" as used herein is meant to refer to substance residues, smears and the like, and is meant to be distinguished from bulk material. A trace amount may be on the order of less than, e.g., 100 μg/cm².

The UV laser light interacts with the target surface and surface deposited chemical. The return light consists of Rayleigh scattered and Raman scattered light from the surface and the target chemical. In parallel with the UV laser, a rangefinder 40 detects the range from the system to the interrogated surface. Data from the rangefinder 40 can be used by control electronics 50 to control the beam conditioning optics 30 and, via an autofocus control module 60, the focus of the receiving telescope 70.

The telescope 70 receives the Rayleigh and Raman scattered light and focuses it first onto optical filtering and beam shaping or conditioning module 80. The optical filtering component filters the Rayleigh scattered (basic UV laser light) and focuses the resulting filtered light onto the end of a fiber optic bundle 90. The near end of the fiber optic bundle is arranged in a nearly round configuration to maximize coupling. The far end, the end closest to a spectrograph 100 is preferably arranged in a linear array of individual fibers, fashioning a slit. Depending on the specific design, the linear array may be arranged in a shallow v-arrangement to offset optical effects that occur in the spectrograph 100. The spectrograph 100 uses a grating and optical components to disperse the received light into its constituent wavelengths and focus the light onto a Charge Coupled Device or other array detector, referred to generally as camera 110. Camera 110 may be an intensified CCD (ICCD) in order to amplify the Raman return signal. The camera 110 converts the optical signal into an electrical waveform that represents the amplitude of the light in each wavelength bin. This signal is then processed and compared against a library of signatures in an analysis computer 120. Processing may include removal of any residual baseline from the received signal and pre-conditioning the library spectra with the system's spectral response so that the measured signal and library spectra appear to have been measured by the same system. When the analysis computer 120 determines a match, it provides the operator with visual, audible, and/or textual notification (indicated by reference numeral 130) indicating the presence, name, etc. of the detected material.

The scene to be analyzed may be viewed using a video camera 140. The system illuminates the telescope's field of view using a designator 150, which indicates to the system operator the interrogation area. In some applications the beam of the range finder 40 may be used as the designator. The operator directs the system to scan the area of interest using a scan control computer 160 that controls the overall scanner 170. Scanning may be accomplished either manually while watching the video scene or the operator can designate an area on the video display which he wishes to scan. The scan control computer 160 then calculates the scanning path of the UV laser 10 and telescope 70. Scanning can also be used as part of mapping functionality to map an area of interest in regard to the presence of one or more target substances.

As will be appreciated by those skilled in the art, this system can be used to remotely interrogate surfaces for specific chemicals, including explosives and their precursors. Other chemicals could also be detected if their spectra are included in the active library used by the algorithm. In one possible implementation, the system may be deployed on a movable or mobile vehicle.

An important aspect of embodiments described herein is the selection of the laser light wavelength. Minimizing interference from fluorescence on real-world backgrounds, while simultaneously avoiding sample degradation, was determined to be a primary driver for selecting a suitable laser wavelength in a system that does not use more complicated fast gating detectors. Phenomenology studies were undertaken to spectroscopically characterize explosives on real-world backgrounds, including 32 vehicle panels (several of which are listed in the table below). As will be discussed in more detail below, laser excitation at 248 nm adequately minimizes fluorescence-interference and sample-degradation.

Raman responses from several explosives were surveyed using laser excitation between 225 and 275 nm. It was concluded that excitation near 257 nm might be well-suited for detecting explosives residues for the following reasons:

1) Preliminary data recorded from a few randomly selected vehicle panels indicated that fluorescence generated by laser excitation at wavelengths longer than 257 nm would greatly reduce sensitivity towards trace explosives.

2) Simple predictions indicated that the strength of the Raman signal favored longer excitation wavelengths, with 257 nm being near the maximum for some of the explosives tested.

3) Strongly absorbing samples tended to yield Raman signatures that showed evidence for photodegradation when recorded with laser wavelengths shorter than 257 nm.

Figure 2:
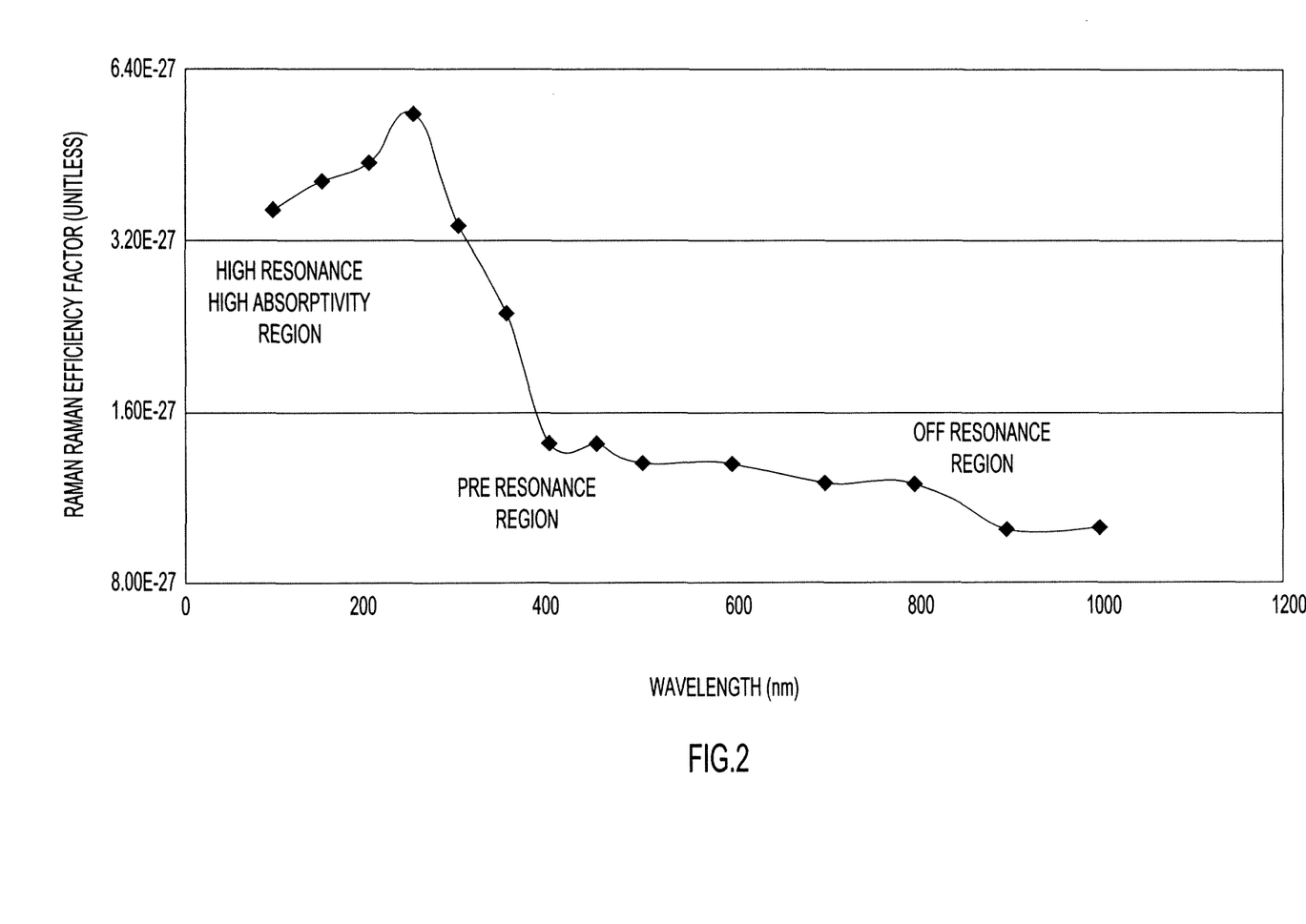
FIG. 2 depicts a plot of Raman photon efficiency factor including three identified resonance regions.

These factors generally describe the "Raman photon efficiency factor," which is the Raman signal strength divided by excitation wavelength. While Albrecht theory can predict the wavelength for highest Raman cross section, this approximation alone fails to take into account the effect of re-absorption and light penetration into the sample on Raman signal strength. FIG. 2, is a plot of the Raman photon efficiency factor, which can be described in 3 regions:

Off Resonance wavelength: Dominance of $v^4$ dependence; minor variances due to molar absorptivity.

Approaching or Pre Resonance: Dramatic increase in Raman scattering & relatively lower increase in molar absorptivity.

High Resonance, High absorptivity: Modest increasing Raman scattering strength relative to molar absorptivity resulting in higher probability of photo/thermal induced change or degradation.

What was found is that as the excitation wavelength approaches resonance, Raman signal strength is balanced by increased scattering strength, but lower photon-molecule interactions. As the excitation wavelength moves closer to optimum resonance, Raman signal strength increasing further is inhibited by much lower photon-molecule interactions to the point at which signal strength is competing with system noise/interference or efficiency. While energetic/explosive materials can be classified in a small set of groups, each material will have a unique Raman photon efficiency profile. Experiments to collect data on signal strength vs. laser wavelength showed that excitation near 257 nm was near the maximum signal possible (theoretically) for explosive materials PETN, and explosive material components UN and AN for samples that were 100 microns thick. Similar data for explosive materials TNT, RDX, and HMX showed a smaller degree of variation for 100-micron samples, but the signal strength was always better at longer wavelengths.

To obtain additional data, further studies compared 257-nm Raman signals of explosives with spectra obtained from randomly selected vehicle panels to determine if fluorescence would severely limit sensitivity. Some of the vehicle panels exhibited overwhelming fluorescence under 257-nm illumination. As such, three additional laser wavelengths were also evaluated: 253 nm, 248 nm, and 244 nm. Because the excitation wavelength was being incremented in small steps ($\Delta\lambda$=4 nm or 5 nm), it was possible to identify a "Raman to Fluorescence Power Ratio" at which the Raman signal was optimal in regard to interfering signals from the background and the Raman photon efficiency factor.

Figure 3A:
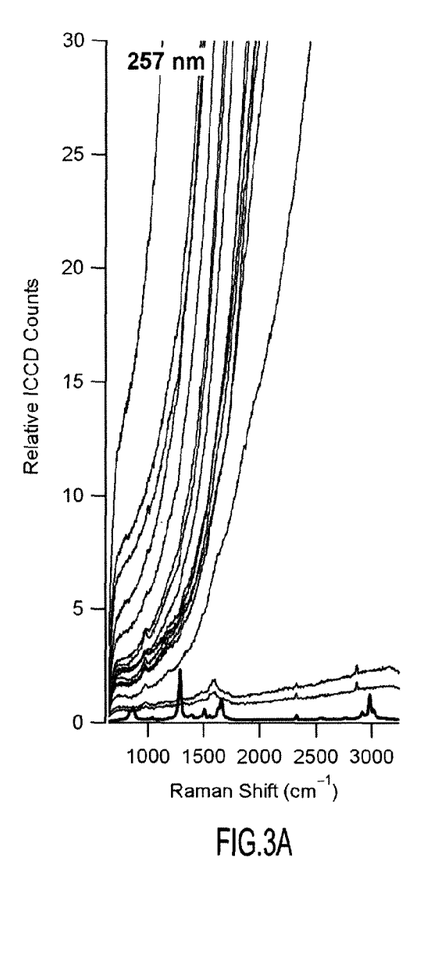
FIG. 3A-C depict plots of fluorescence spectra recorded from vehicle panels used in connection with experiments conducted in accordance with an embodiment of the present invention.
Figure 3B:
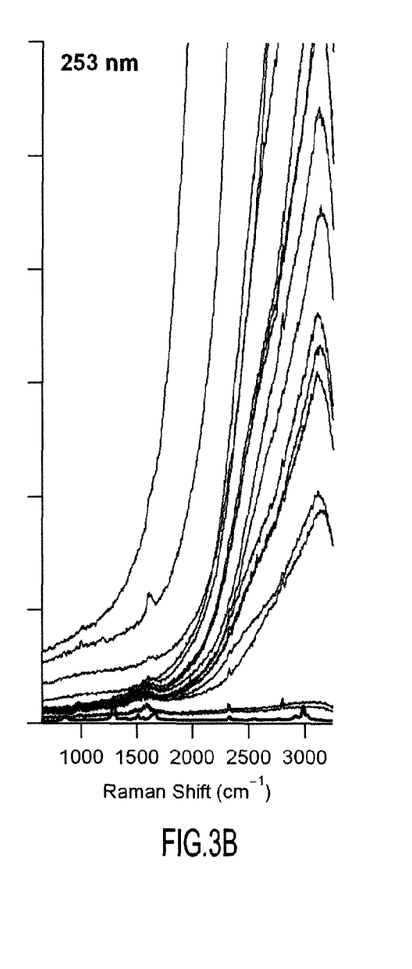
Figure 3C:
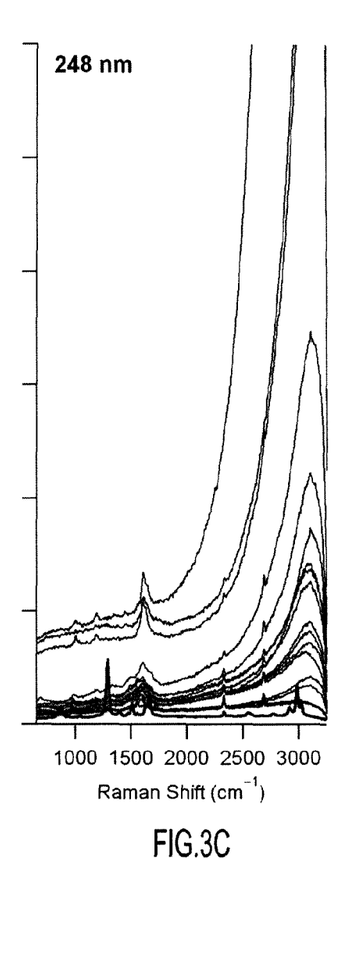
Figure 4A:
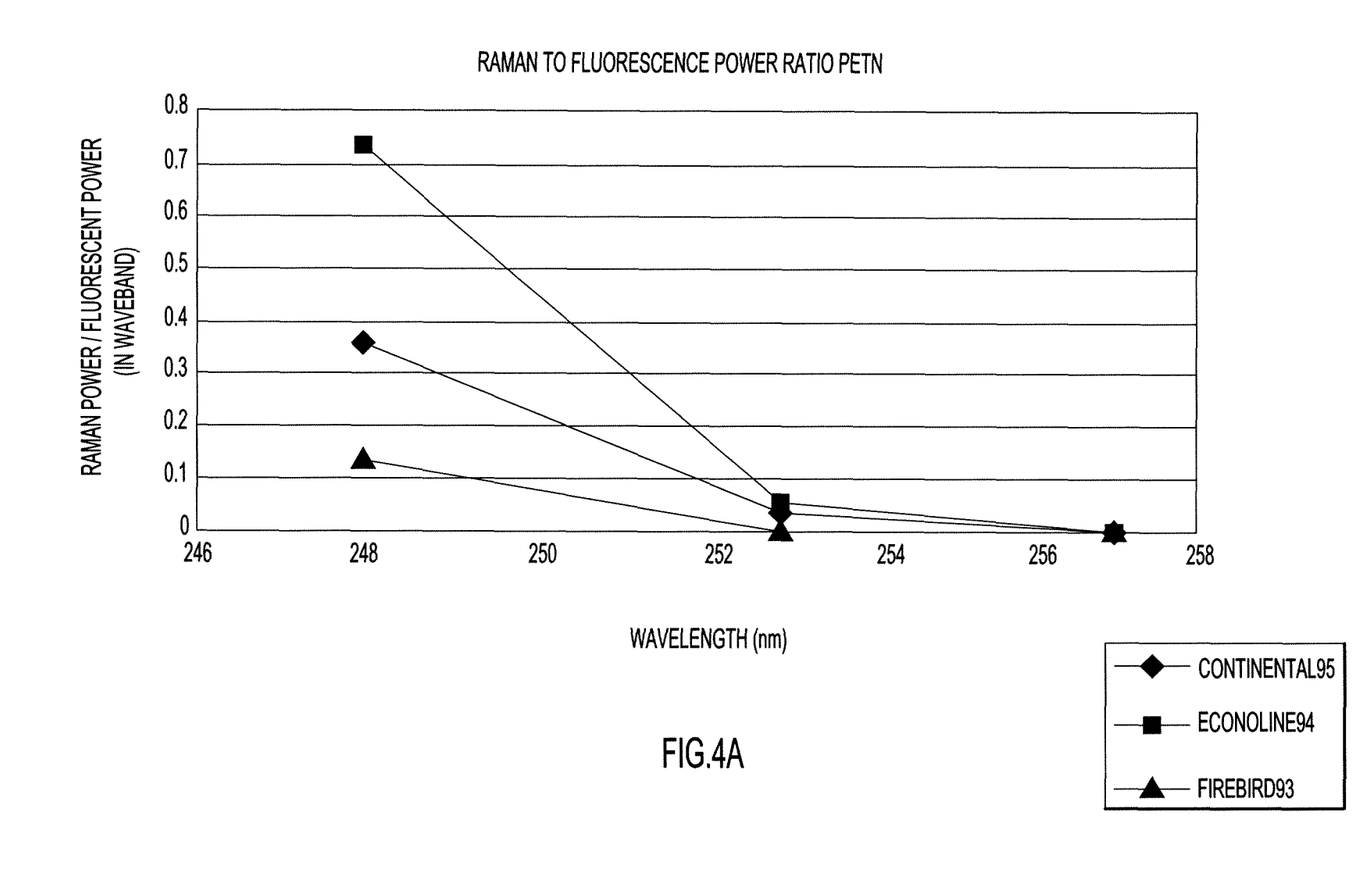
FIGS. 4A and B show Raman to fluorescence power ratio data for explosive material PETN and Semtex.
Figure 4B:
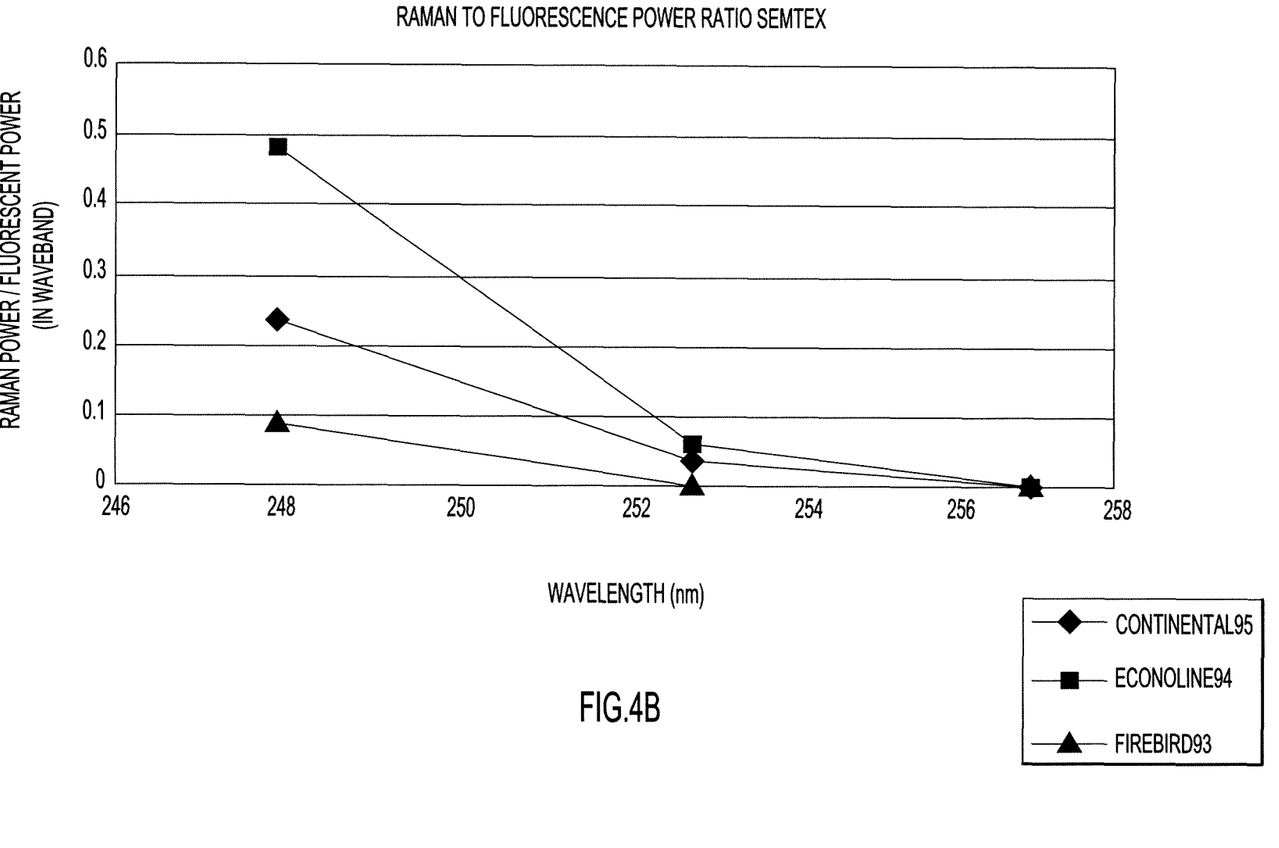

Shown in FIGS. 3A-C are fluorescence spectra obtained from 17 randomly selected painted vehicle surfaces, recorded with a Ti:sapphire laser operating at 257 nm, 253 nm, and 248 nm, respectively. As can be seen, the strength of the observed fluorescence decreases significantly as the excitation wavelength is shifted from 257 nm to 248 nm. Importantly, studies have shown that the intensity of the Raman signal from the explosives of interest do not change as dramatically with excitation wavelength. Thus, the Raman to Fluorescence Power Ratio that is larger with 248-nm excitation is of importance. This point is underscored by the data presented in FIGS. 4A and 4B, which show Raman to Fluorescence power ratios for PETN and Semtex (a formulation including PETN and RDX), respectively, disposed on the indicated vehicle as a background for the explosive material.

Details of vehicles used in experiments described herein include:

| Panel # | Year | Make & Model | Color |
|---|---|---|---|
| 2 | 1995 | Lincoln Continental | dark blue |
| 4 | 1994 | Ford Econoline | silver |
| 5* | 1994 | Ford Thunderbird | teal |
| 15* | 1993 | Pontiac Firebird | orange |
| 31* | 1995 | VW Jetta | red |
| 32* | 1991 | Jaguar X86 | burgundy |

Panels from vehicles denoted by an asterisk are employed in separate experiments as discussed further below.

The Raman to Fluorescence Power ratios in the waveband of interest was derived by computing absolute spectrum variance over the Raman signal waveband of 700-2000 wavenumbers ($cm^{-1}$). It is of note that including the Carbon-Hydrogen bond (CH) region of the signature (waveband 2000-3000) would decrease values even further, but the predominant information used in detecting and identifying the explosive residue is contained in the waveband used and therefore a better system design metric.

Experiments have shown the ability to detect TNT, PETN, and AN at concentrations as low as 3-50 $\mu g/cm^2$ from a standoff distance of 10 meters using moderate laser power (~100 mW). Notably, positive detections were reported for samples containing masses as low as 45 $\mu g$ of PETN, 5 $\mu g$ of RDX, and 500 ng AN.

Figure 5A:
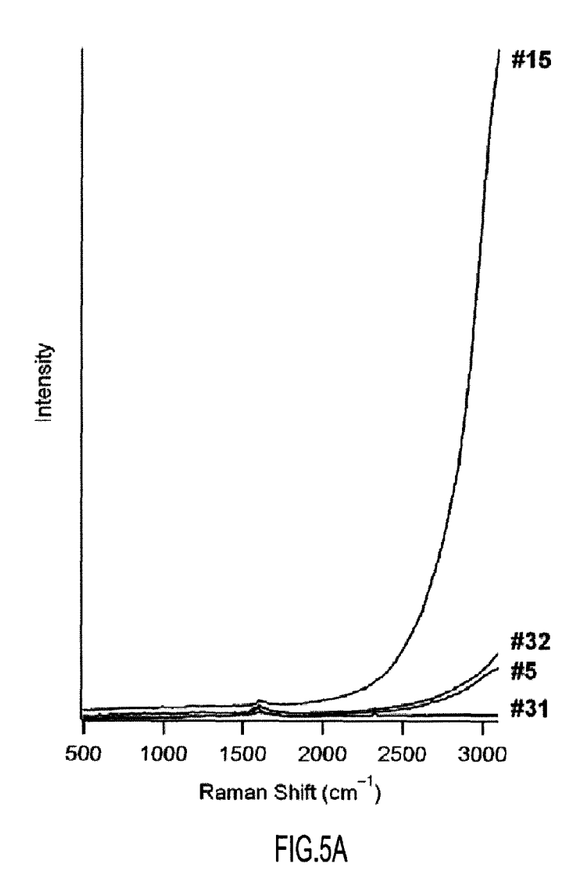
FIGS. 5A and 5B depict plots of spectra of selected vehicle panels used in connection with experiments conducted in accordance with an embodiment of the present invention.
Figure 5B:
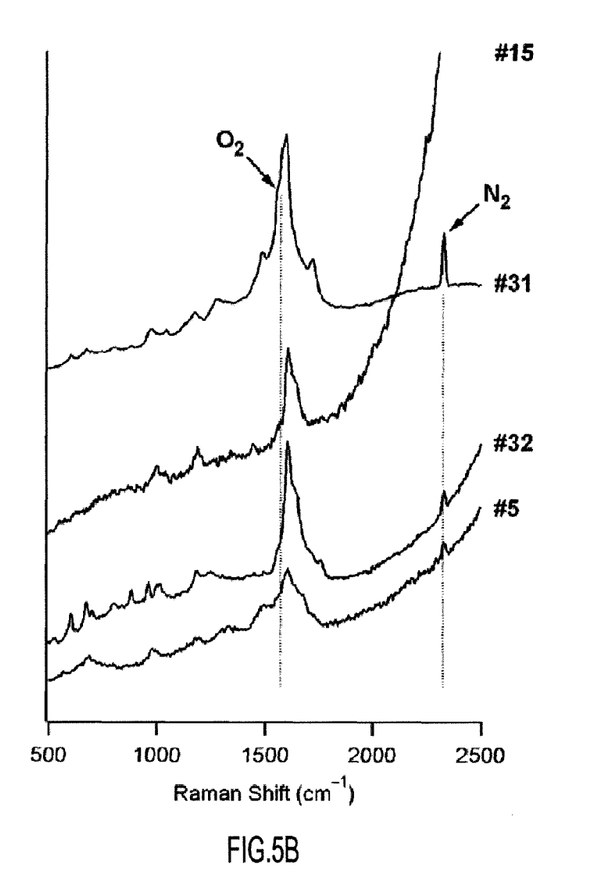
Figure 6A:
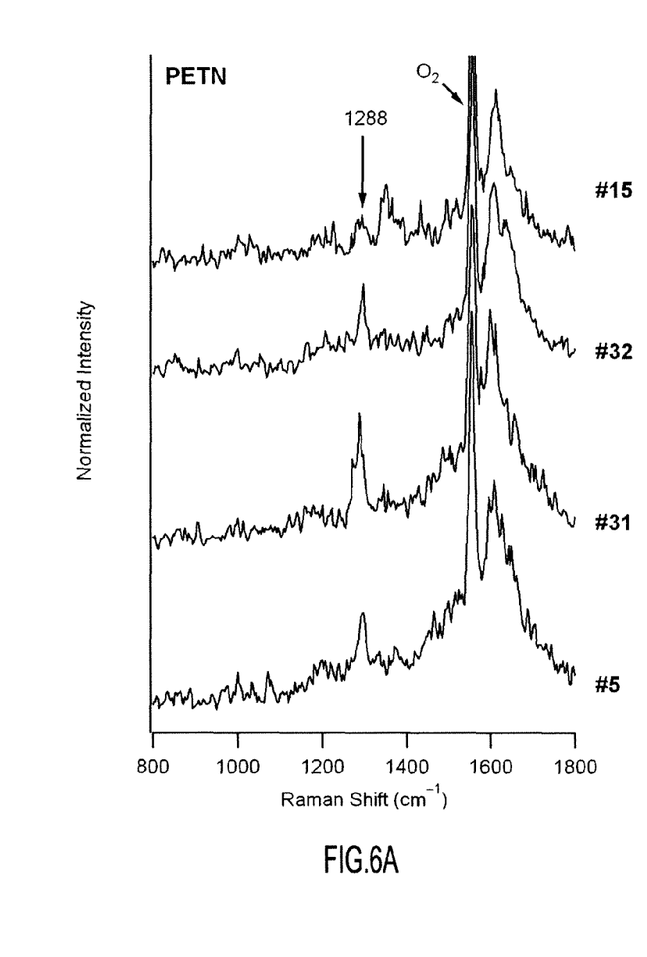
FIGS. 6A and 6B depict plots of the Raman shift for PETN and TNT using 248-nm excitation at a 10 meter standoff.
Figure 6B:
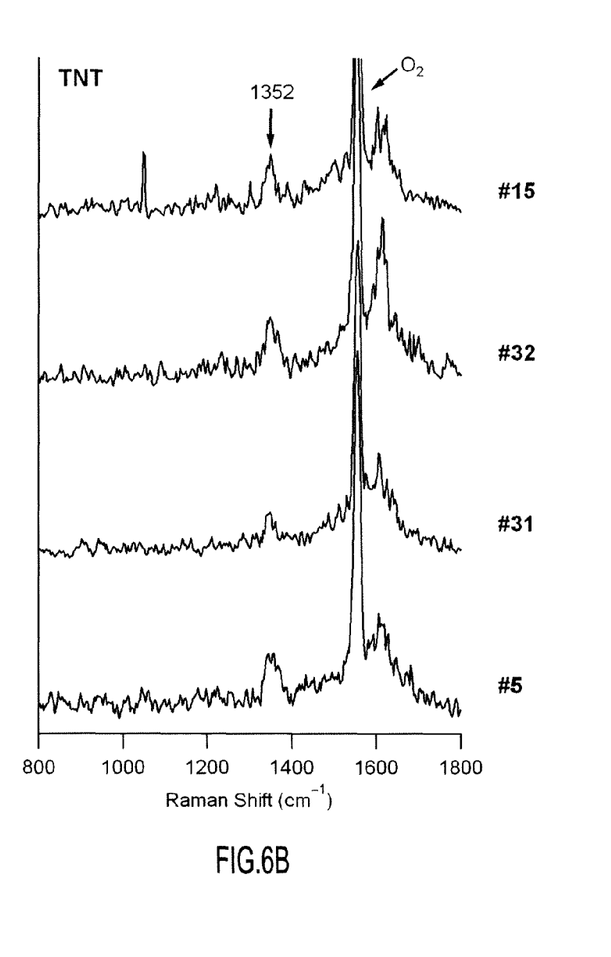

More specifically, vehicle panels #5, #15, #31, and #32 (see table above) were randomly selected for testing with deposited explosive residues. The spectra obtained from these panels are shown in FIGS. 5A and 5B. This set of Raman spectra qualitatively represents the four types of spectra that were observed. Note that the intensity of the recorded signal from vehicle panel #15 was found to be considerably stronger than other vehicle panels. The spectrum of #31 has been vertically offset in FIG. 5B for clarity. Raman bands attributable to ambient nitrogen and oxygen are marked. The oxygen Raman band is obscured by overlap with Raman bands from each surface.

Figure 7A:
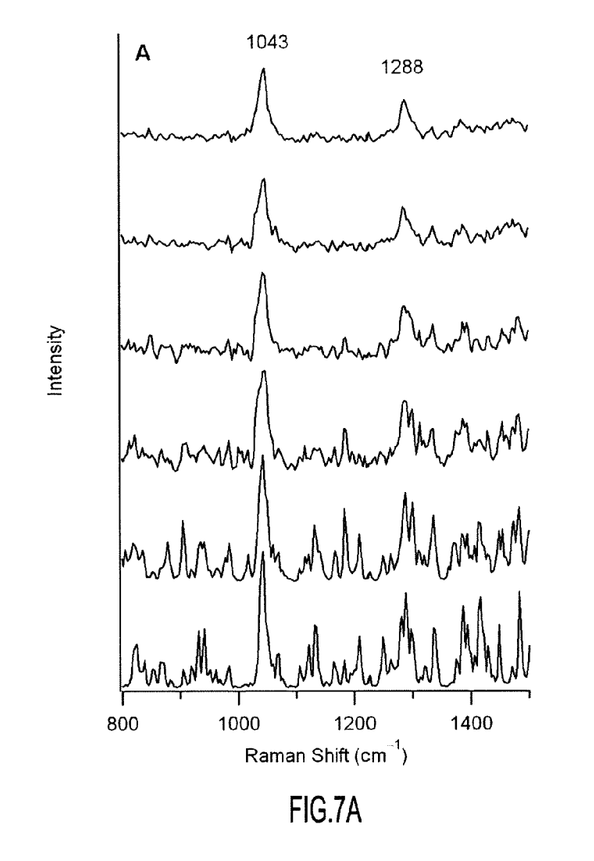
FIGS. 7A and 7B depict plots of the Raman shift for AN residues on aluminum-coated glass and a surface of a vehicle panel in connection with methodologies according to an embodiment of the present invention.
Figure 7B:
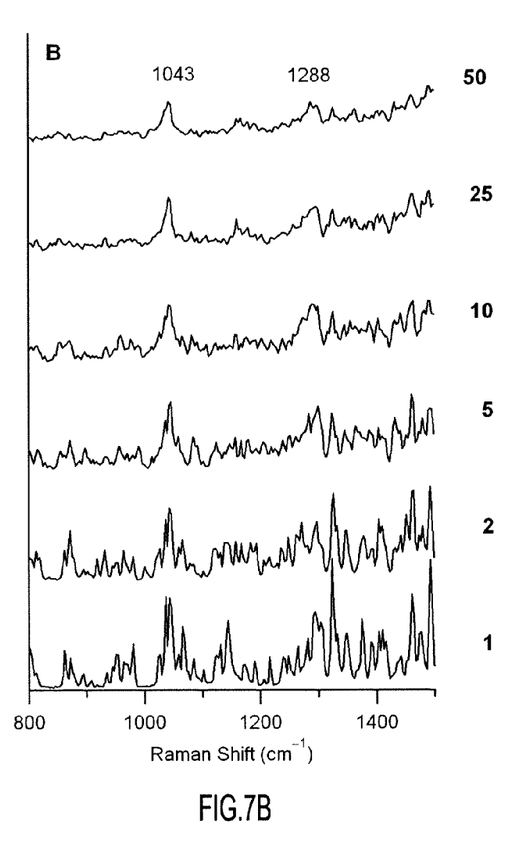

Shown in FIGS. 6A and 6B and FIGS. 7A and 7B are spectra obtained from residues of PETN (FIG. 6A), TNT (FIG. 6B) and AN (FIGS. 7A and 7B) deposited onto various surfaces at 10-meter standoff using 248-nm excitation. Each spectrum shown in FIGS. 6A and 6B corresponds to the average of 25 contiguous acquisitions (for a total integration time of 850 msec), and those in FIGS. 7A and 7B correspond to varying amounts of signal averaging. More specifically, FIG. 7A depicts UV spectra of AN residues on aluminum-coated glass, and FIG. 7B shows a plot of vehicle surface #31. The corresponding number of acquisitions, each 34 msec in duration, is shown on the right-hand side of FIG. 7B. Traces have been vertically offset for clarity. Estimated surface concentrations of AN for FIG. 7A and FIG. 7B were ~10 $\mu g/cm^2$ and ~20 $\mu g/cm^2$, respectively, which are barely detectable by the eye.

In all cases it was possible to find a portion of the dataset that yielded signal-to-noise ratios greater than 10 for the prominent band of AN in less than one second of total integration (25 acquisitions).

As noted, embodiments of the present invention employ "deep uv" laser wavelengths, namely those at 250 nm or below. The use of this particular wavelength range is non-trivial, since it has been established that fluorescence at 262 nm, and even perhaps for all wavelengths from 250 nm to 1000 nm, will render detection of trace explosives at significant stand off range (>5 meters) difficult if not impossible.

The Raman sensor described herein also has the capability to interrogate bulk samples of larger than trace amounts.

As mentioned, detectable substances include explosive materials, toxic chemicals, biologicals, and chemical warfare agents, and other materials that have Raman signatures.

The systems and methods described herein may be embodied in other specific forms without departing from the spirit or essential characteristics thereof. The foregoing embodiments are therefore to be considered in all respects illustrative and not meant to be limiting.

What is claimed is:

1. A method of performing Raman spectroscopy, comprising:
    irradiating, with laser light, a trace amount of a target substance disposed on a painted surface;
    receiving reflected laser light and a Raman return signal from the trace amount of the target substance;
    processing the Raman return signal using, at least, a spectrograph and camera to obtain a Raman signature for the target substance; and
    identifying the target substance based on the Raman signature for the target substance and a database of Raman signatures,
    wherein a ratio of a power of the Raman return signal to fluorescence power is at least about 0.1, and
    wherein the ratio of a power of the Raman return signal to fluorescence power is derived by computing absolute spectrum variance over the Raman signal waveband of 700-2000 wavenumbers ($cm^{-1}$).

2. The method of claim 1, wherein the ratio of the power of the Raman return signal to fluorescence power is between 0.1 and 0.5.

3. The method of claim 1, wherein the ratio of the power of the Raman return signal to fluorescence power is greater than 0.5.

4. The method of claim 1, wherein the target substance is located on a panel of a vehicle.

5. The method of claim 1, wherein the laser light has a wavelength of about 248 nm.

6. The method of claim 1, wherein the target substance comprises explosive material residue at a concentration of no more than about 100 $\mu g/cm^2$.

7. The method of claim 1, wherein the target substance comprises explosive material residue at a concentration of no more than about 50 $\mu g/cm^2$.

8. The method of claim 1, wherein the target substance comprises explosive material residue at a concentration of no more than about 5 $\mu g/cm^2$.

9. The method of claim 1, wherein the power of the laser light is about 100 mW.

10. The method of claim 9, wherein the Raman return signal is detected from a standoff distance of at least 10 meters and the target substance is no more than 45 $\mu g$ of pantaerythritol tetranitrate (PETN).

11. The method of claim 9, wherein the Raman return signal is detected from a standoff distance of at least 10 meters and the target substance is no more than 5 $\mu g$ of cyclorimethylene trinitramine (RDX).

12. The method of claim 9, wherein the Raman return signal is detected from a standoff distance of at least 10 meters and the target substance is no more than 500 ng of ammonium nitrate (AN).

13. A method, comprising:
    irradiating, with laser light, a trace amount of a target substance disposed on a painted surface;
    receiving reflected laser light and a Raman return signal from the trace amount of the target substance; and processing the Raman return signal using, at least, a spectrograph and camera to obtain a Raman signature for the target substance;

wherein a wavelength of the laser light is 248 nm and a ratio of a power of the Raman return signal to fluorescence power is at least about 0.2, and wherein the ratio of a power of the Raman return signal to fluorescence power is derived by computing absolute spectrum variance over the Raman signal waveband of 700-2000 wavenumbers ($cm^{-1}$).

14. The method of claim 13, wherein the target substance is disposed on a panel of a vehicle.

15. The method of claim 13, wherein the power of the laser light is about 100 mW.

16. The method of claim 13, wherein a standoff distance between a laser emitting the laser light and the target substance is about 10 meters.

17. The method of claim 16, wherein the target substance is no more than 45 μg of pantaerythritol tetranitrate (PETN).

18. An apparatus, comprising:
   a laser that produces laser light at a wavelength of 248 nm;
   a telescope configured to receive a Raman return signal from a trace amount of a target substance excited by the laser light;
   a spectrograph configured to disperse the Raman return signal received via the telescope into its constituent wavelengths and generate a corresponding optical signal; and
   a camera, in communication with the spectrograph, configured to convert the optical signal output from the spectrograph into an electrical signal,
   wherein, when the apparatus is in use, a ratio of a power of the Raman return signal to fluorescence power is at least about 0.1, and
   wherein the ratio of a power of the Raman return signal to fluorescence power is derived by computing absolute spectrum variance over the Raman signal waveband of 700-2000 wavenumbers ($cm^{-1}$).

19. The apparatus of claim 18, further comprising an analysis computer configured to compare the electrical signal to respective ones of Raman signatures stored in a library and to identify the target substance.

20. The apparatus of claim 18, wherein the power of the laser light is about 100 mW.

* * * * *